(12) United States Patent
Wischerhoff et al.

(10) Patent No.: US 6,472,224 B1
(45) Date of Patent: Oct. 29, 2002

(54) BIOSENSOR WITH MODIFIED PRECIOUS METAL SURFACE AND PROCESS FOR THE PREPARATION THEREOF

(75) Inventors: Erik Wischerhoff; Thomas Nicolaus, both of München (DE)

(73) Assignee: Franz Schleicher, Ingolstadt (DE)

( * ) Notice: Subject to any disclaimer, the term of this patent is extended or adjusted under 35 U.S.C. 154(b) by 0 days.

(21) Appl. No.: 09/292,555

(22) Filed: Apr. 15, 1999

(30) Foreign Application Priority Data

Apr. 17, 1998 (DE) .......................................... 198 17 180
Nov. 19, 1998 (DE) .......................................... 198 53 428

(51) Int. Cl.[7] .......................... G01N 33/48; G01N 27/26
(52) U.S. Cl. ................. 436/166; 422/82.05; 422/82.11; 435/4; 435/817; 204/414
(58) Field of Search ..................... 422/82.05, 82.11; 436/164, 166; 435/287.1, 4, 817; 204/403.1, 414

(56) References Cited

FOREIGN PATENT DOCUMENTS

| EP | 485 874 B1 | 5/1992 |
| EP | 485 874 A2 | 5/1992 |
| EP | 589 867 B | 4/1994 |
| WO | WO 97/41425 | 11/1997 |

OTHER PUBLICATIONS

Kosswig et al., Eds., "Die Tenside," Carl Hanser Verlag, Munich, Table of Contents and pp. 2–7 (1993) (one page English language summary included).
Elender, Thesis, Technical University of Munich, (translation included) pp. 113–115 (1996).
Ichinose et al., "Stepwise Adsorption of Metal Alkoxides on Hydrolyzed Surfaces: A Surface Sol–Gel Process," *Chemistry Letters* 831–832 (1996).
Kretschmann et al., "Radiative Decay of Non–Radiative Surface Plasmons Excited by Light," *Z. Naturforsch* 23:2135–2136 (1968).
Piehler et al., "Surface modification for direct immunoprobes," *Biosensors & Bioelectronics* 11:579–590 (1996).
Tasker et al., "Molecular Resolution Imaging of Dextran Monolayers Immobilized on Silica by Atomic Force Microscopy," *Langmuir* 12:6436–6442 (1996).

*Primary Examiner*—Lyle A. Alexander
(74) *Attorney, Agent, or Firm*—Mueting, Raasch & Gebhardt, P.A.

(57) ABSTRACT

The present invention relates to a biosensor (affinity sensor) in which a hydrogel, a surfactant layer or biotin are bonded to the biosensor's precious metal surface by means of a short-chained linker, as well as to the process for the preparation thereof. A complete covering of the biosensor surface with the hydrogel, the surfactant layer or the biotin is achieved by hydrogen bonds, aromatic-aromatic interactions or by covalent bonds.

22 Claims, 3 Drawing Sheets

BIOSENSOR WITH MODIFIED PRECIOUS METAL SURFACE AND PROCESS FOR THE PREPARATION THEREOF

This application claims priority to German Patent Application Nos. 198 17 180.3-52 (filed Apr. 17, 1998 and issued Apr. 27, 2000 as German Patent No. DE 198 17 180) and 198 53 428.0 (filed Nov. 19, 1998), which are hereby incorporated herein by reference in their entirety.

BACKGROUND OF THE INVENTION

This invention relates to a biosensor (affinity sensor) in which a hydrogel, a surfactant layer or biotin is bonded to the sensor's precious metal surface by a short chain linker, and further relates to the procedure for the preparation thereof.

For signal generation, the surfaces of surface plasmon resonance (SPR) based affinity sensors must possess a precious metal layer, usually of gold, with a thickness of approx. 50 nm. However, direct bonding of receptors, typically proteins, to the precious metal surface has proven to be impractical because the receptors are easily denatured in this environment and as a result lose their receptor function. Also, bare sections of the precious metal surface can be subject to unspecific adsorption phenomena which seriously flaw the measurement results.

To avoid this problem, it is general practice to covalently bond to the precious metal surface a several nm thick dextran layer that swells in an aqueous medium to a thickness of approx. 100 nm and completely covers the precious metal surface. The swollen polymer layer mimics the natural environment of biomolecules and is thus suited to prevent the denaturation and the resulting inactivation of the receptors. The adsorption of molecules other than those to be analyzed is effectively suppressed. In addition, the swollen dextran layer is able to compensate surface irregularities: the bonding of receptor molecules occurs in the swollen matrix and not only immediately on the surface. This reduces the significance of surface roughness that would otherwise result in a poorly defined surface and thus in poorly quantifiable measurement results.

Coatings are known which can be applied to sensor surfaces to both prevent unspecific adsorption and to serve as a matrix for the receptor molecules (Molecular Resolution Imaging of Dextran Monolayers Immobilized on Silica by Atomic Force Microscopy, Langmuir, 1996, 12, 6436). However, such surfaces often possess defect sites resulting from their molecular structure and therefore do not provide sufficient protection against unspecific adsorption.

EP-B-589 867 describes a biosensor measuring surface in which a porous matrix, e.g. a hydrogel such as dextran, is bonded to a metal surface via a monolayer of organic molecules (linkers). Such coatings are used in the preparation of disposables for commercial SPR sensors. To ensure complete covering of the biosensor's surface with the porous matrix and sufficient stability, EP-B-589 867 specifies that molecules having a hydrocarbon chain with a length of more than 10 atoms be used as linkers. The linker's functional groups to which the porous matrix is bonded are hydroxyl, carboxyl, amino, aldehyde, hydrazide, carbonyl, expoxide or vinyl groups. The preferred linker is 16-mercaptohexadecanol, the hydroxyl group of which must by activated by a reaction using epichlorhydrin before the bonding of dextran to the sensor surface. EP-B-589 867 does not make any statements on the conditions of further reactions of the other functional groups with a porous matrix, The necessity for using long-chained linkers to bond the porous matrix to the precious metal surface is a disadvantage, given the time and effort required to prepare such compounds. A further disadvantage is the use of the toxic and carcinogenic epichlorhydrin for the activation of the linker's functional group.

SUMMARY OF THE INVENTION

Therefore, the object of the present invention is to provide a biosensor with a modified precious metal surface in which a hydrogel, a surfactant layer or biotin is linked to the precious metal surface by less complex and, if possible, commercially available linker molecules.

A further object of the invention is to provide a process for the preparation of the above biosensor with a modified precious metal surface which is less expensive and easier to implement than the state-of-the-art procedures.

These aims could be accomplished owing to the finding that even with the use of linker Molecules having a hydrocarbon chain length of 10 atoms or less, a complete covering of the precious metal surface with a hydrogel, a surfactant layer or biotin can be achieved if the linker molecule monolayer is stabilized by hydrogen bonds, aromatic-aromatic interactions or covalent bonds.

The present invention thus refers to a biosensor the surface of which comprises a precious metal layer to which a hydrogel, a surfactant layer or biotin is bonded by means of a monolayer of organic molecules, whereby said employed organic molecules used for this have the formula A—R—B in which A is an atom or group providing the bonding to the precious metal; R is a branched or straight hydrocarbon chain with a chain length of 10 carbon atoms or less, whereby the hydrocarbon chain may be interrupted in up to two places each by a phenylene group or an heteroatom, and B is an atom or group providing the bonding to the hydrogel, the surfactant layer or the biotin.

The invention also provides a process for the preparation of the aforesaid biosensor in accordance with one of the claims 12 to 15.

The inventive biosensors with a modified precious metal surface are preferably used for surface plasmon resonance (SPR) applications.

In order to prevent unspecific adsorption of receptor molecules, the surface of the biosensor must be completely covered with hydrogel, a surfactant layer or biotin. One prerequisite for a stable hydrogel, surfactant or biotin layer is sufficient stability of the linker molecule layer underneath. Such stability can be ensured by hydrogen bonds, by aromatic-aromatic interactions ($\pi$-$\pi$ interactions) or by covalent bonds, which may be provided by an interlayer containing metal oxide. Such interactions or bonds occur between the linker molecules or between the linker molecules and the hydrogel, the surfactant or the biotin.

Hydrogen bonds may exist between amide bonds (e.g. B=amine group; carboxyl-functionalized hydrogel) or between hydroxide and carboxyl groups (e.g. B=epoxide group; carboxyl-functionalized hydrogel). In systems where hydrogen bonds exist, such hydrogen bonds may be formed between the linker modules and the hydrogel, the surfactant layer or the biotin, where they serve for bridging or preventing local defects.

Aromatic-aromatic interactions are observed between aromatic ring systems in the linker molecules. Such interactions are the source of attraction forces between the linker molecules which stabilize the monolayer. Suitable aromatic groups are phenylene groups, and in particular those phenylene groups that are incorporated in the linker molecule in para position. The phenylene groups may be substituted with small, non-bulky alkyl groups such as methyl or ethyl groups.

Another possibility to provide a stable linker molecule layer is the introduction of covalent bonds. In a preferred embodiment, the first step after bonding of a low molecular weight short-chained linker of the present invention is to build up, preferably by a sol-gel process, a dense interlayer comprising metal oxide (Stepwise Adsorption of Metal Alkoxides on Hydrolyzed Surfaces: A Surface Sol-Gel Process, Chemistry Letters, 1996, 831); which in a second step is linked to the hydrogel, the surfactant or the biotin by means of the hydroxide groups contained in it (Surface Modification for Direct Immunoprobes, Biosensors and Bioelectronics, 1996, 11, 579; Dissertation of G. Elender, Technical University of Munich, 1996, p. 113). These three references are incorporated herein by reference.

The state of the art is the stabilization of the linker molecule layer by the use of linkers with long alkyl chains that provide a dense and stable layer due to crystallization of the alkyl chains (EP-B-589 867).

One important advantage of a layered structure that makes use of hydrogen bonds or aromatic-aromatic interactions is the fact that it is very easy to prepare. On the other hand, layered structures using a metal oxide interlayer are more complex to prepare but offer the possibility of precisely controlling the layer thickness of the overall system, optionally by performing several consecutive sol-gel process steps. The layer thickness allows in turn to influence the minimum position relating to the surface plasmon resonance signal, which may be desirable from a measurement point of view.

DETAILED DESCRIPTION OF THE INVENTION

The biosensor of the present invention comprises a layer of precious metal, which may be e.g. silver or gold in terms of the invention. The film has a thickness between 30 and 70 nm, preferably between 40 and 60 nm.

The linker molecules used are short-chained organic A—R—B molecules with an atom or group A providing the bonding to the precious metal. Preferred substances are thiols, disulfides, selenides and diselenides with an additional functional group. The linker molecule has a branched or straight hydrocarbon chain with a chain length of up to 10 carbon atoms, which can be interrupted in up to two places each by a phenylene group or a heteroatom such as —O— or —NH—. The heteroatoms and/or the carbons of the phenylene groups are not considered for the calculation of the chain length. The hydrocarbon chain has preferably a length of up to 6 carbon atoms. The hydrocarbon chain is preferably of the straight type.

Thiols and disulfides being less expensive than the equivalent selenium compounds, they are preferably used in the inventive biosensors having a modified precious metal surface.

The linker molecule's second functional group B provides the bonding with the hydrogel, the surfactant or the biotin, or the bonding with the dense metal oxide layer. In principle, all known state-of-the-art B groups may be used, e.g. hydroxyl, carboxyl, epoxide or amino groups. In the case of the interlayer comprising metal oxide, preference is given to hydroxyl groups, whereas in the case of direct bonding of the hydrogel, the surfactant or the biotin to the low molecular weight linker the use of epoxide or amino groups is particularly preferred.

All known surfactants are suitable as surfactants (cf.: Die Tenside, published by: K. Kosswig, H. Stracke, C. Hauser Verlag, Munich, 1993 which is incorporated herein by reference). For example, surfactants with an anionic group, such as carboxylates, sulfonates, sulfates, ether sulfates, phosphates, phosphites, phosphonates, phosphinates and thiosulfates are suitable. Carboxylates, phosphonates and sulfonates are particularly preferred. Alkali metal ions and ammonium ions $NH_4^+$ are suitable counterions for anionic surfactants. Surfactants with a cationic group, such as ammonium salts, pyridinium salts and sulfonium salts, are also suitable. Particularly preferred cationic surfactants are quaternary ammonium salts. Counterions of cationic surfactants are mainly halides, especially chloride. Surfactants with zwitterionic groups are also suitable for the surfactant layer of the present invention. Examples are amino carbonic acids, betains, sulfobetains and lecithins (e.g. phospholipids). Among the zwitterionic surfactants, lecithins are particularly preferred. All surfactants have in addition to the aforementioned hydrophilic group a hydrophobic group which may be e.g. $C_nH_{2n+1}$—, $C_nH_{2n-1}$—, $C_nH_{2n+1}$—$C_6H_4$—, $C_nF_{2n+1}$ or $H_3C(-Si(CH_3)_2-O)_m$—. Except in the case of silicone surfactants, the hydrophobic groups usually have between 6 and 22 carbon atoms. With silicone surfactants, n is usually between 4 and 20.

Biotin-functionalized biosensor surfaces are suited for the selective determination of streptavidin.

The hydrogel used may be a polysaccharide, a polysaccharide derivative or a swellable organic polymer such as poly{N-[tris-(hydroxymethyl)-methyl]acrylic acid amide}, polyvinyl alcohol or polyethylene glycol. Poly{N-[tris-(hydroxymethyl)-methyl]acrylic acid amide} and polyethylene glycol are preferred.

Examples of polysaccharides are amylose, inulin, pullulan or dextran. Preferred polysaccharides are pullulan and dextran, in particular dextran.

In order to facilitate the bonding of the hydrogel to the linker modules, the hydrogel may be derivatized to comprise e.g. hydroxyl, carboxyl, amino or carbonyl groups. Carboxymethyl-derivatized hydrogel is particularly preferred.

Two preferred embodiments are given to explain the present invention in more detail. In the first embodiment, the hydrogel, the surfactant layer or the biotin is bonded directly to the linker molecules, i.e. without the introduction of further atoms between the hydrogel, the surfactant layer or the biotin and the linker molecules. Reaction scheme 1 shows an example of this. In a first step, a monolayer of aminothiol is applied to the precious metal surface. In a second step, a carboxyalkyl-derivatized polysaccharide is bonded directly to this linker molecule monolayer by means of amide bonds.

The amide bonding is typically performed using ethyl-3-dimethylamino-propyl-carbodiimide and N-hydroxysuccinimide. After this step, the functionalization is completed to such an extent that the end user can perform the bonding of receptor molecules.

Reaction Scheme 1

In this embodiment, only two steps are required to prepare a carboxyalkylated polysaccharide surface. Moreover, there is no need to use highly toxic and carcinogenic substances. A highly concentrated polymeric solution is not required. A further advantage is the fact that only aqueous solutions are used in this embodiment.

In a second preferred embodiment, the hydrogel, the surfactant layer or the biotin are bonded to the linker molecules by means of a metal oxide interlayer. Reaction scheme 2 shows an example of this. In a first step, a hydroxythiol monolayer is bonded to a precious metal layer. These linker molecules are then reacted with a metal alkoxide, preferably Ti(IV)butoxide. A hydrolysis is then performed to obtain a hydroxy-functionalized surface. The chemical reactivity of the metal oxide layer obtained in this way is equivalent to that of purified glass. It is now possible to bond e.g. an expoxy silan to the hydroxy groups, which in turn allows the bonding of a hydroxy polymer. The hydroxy polymers used may be polysaccharides or synthetic polymers containing hydroxy groups, such as dextran or its derivatives, polyvinyl alcohol, pullulan and poly{N-[(tris-(hydroxymethyl)-methyl]acrylic acid amide}. To facilitate the bonding of surfactants or biotin, the metal oxide-comprising interlayer should preferably be derivatized with N-hydroxysuccinimide. The metal oxide-comprising interlayer should preferably essentially completely consist of metal oxide.

Reaction Scheme 2

To prepare a biosensor surface according to the present invention, a glass support with a vapor deposited gold layer is placed in a, preferably aqueous, solution of linker molecules of the present invention. The duration of this functionalization is between 2 h and 24 h, typically 12 h. The temperature can be between 15° C. and 35° C. The concentration of linker molecules in the solution ranges from $5 \cdot 10^{-4}$ to $2 \cdot 10^{-1}$ mole·l$^{-1}$, preferably from $5 \cdot 10^{-3}$ to $5 \cdot 10^{-2}$ mole·l$^{-1}$.

The intermediate product thus produced has a monolayer of organic linker molecules of the invention. The hydrogel, the surfactant layer or the biotin may be bonded to it directly or by means of a metal oxide-comprising interlayer.

For direct bonding of the hydrogel, the surfactant or the biotin to the linker molecule monolayer, the support is placed for 1 h to 5 h, typically 3 h, into a respective freshly prepared aqueous solution. The concentration is between 10 and 50 mg·ml$^{-1}$. The hydrogel may optionally be derivatized according to known methods.

To produce a metal oxide interlayer, on the other hand, the first step is to prepare a metal alkoxide solution of metal alkoxide, water and organic solvents such as ethanol or toluol. The metal oxide layer can be prepared e.g. using titanium(IV)butoxide, tetramethoxy silan, aluminum(III) butoxide, zirconium(IV)propoxide or niobium(V)butoxide. The preferred substance is titanium(IV)butoxide. The intermediate product is then immersed into this metal alkoxide solution for 5 to 20 minutes.

To allow the bonding of the hydrogel, the metal oxide layer thus obtained should be functionalized. This can be done by known methods using epoxy silan compounds such as (3-(2,3-epoxypropoxy)propyl)triethoxy silan. This functionalization step can be performed at room temperature and lasts between 10 and 40 minutes.

The bonding of a hydroxy polymer is performed in a similar way as with the first embodiment, except that the duration of immersion in the hydroxy polymer solution is extended to between 12 and 48 h, typically 24 h.

A more detailed explanation of the present invention is given in the following examples.

EXAMPLES

Example 1
Preparation of the Functionalized Surface
A gold-coated glass support (film thickness: approx. 50 nm) is immersed for 12 h into a $2 \cdot 10^{-2}$ mole·l$^{-1}$ aqueous solution of cysteaminium hydrochloride. After rinsing with 100 ml of ultrapure water and 10 ml of 0.1 mole·l$^{-1}$ NaOH, the support is placed for 3 h into a solution of 22 mg of sodium salt of carboxymethyldextran (Fluka), 77 mg of ethyl-3-dimethylamino-propyl-carbodiimide (EDC) and 12 mg of N-hydroxysuccinimide (NHS) in 1 ml of ultrapure water. After this, the support is rinsed three times with 20 ml of ultrapure water.

The carboxymethyl-functionalized sensor is mounted in an SPR instrument. The SPR instrument used is designed by the inventor and is of the $\theta/2\theta$ type (in analogy to E. Kretschmann and H. Raether, "Radiative Decay of Non-Radiative Surface Plasmons Excited by Light", Z. Naturforsch., Vol. 23a, p. 2135 (1968) which is incorporated herein by reference), that is equipped with an infrared laser (wave length 784 nm) as its light source.

Figure 1:
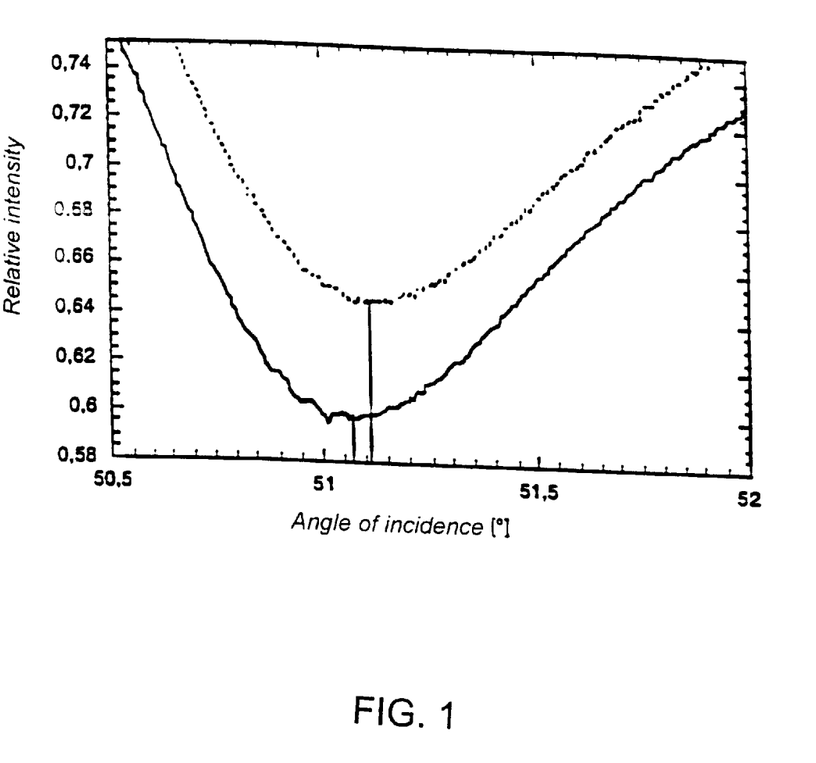
FIG. 1 shows the surface plasmon resonance curves before and after the bonding of carboxymethyldextran to an amino-functionalized gold surface.

FIG. 1 shows the measurement of the surface plasmon resonance after the amino-functionalization (solid line) and after bonding of the carboxymethyldextran (dashed line).

The displacement of the minimum towards a higher incidence angle serves as an indicator for the growth of the layer in thickness.

Bonding of a Protein

Figure 2:
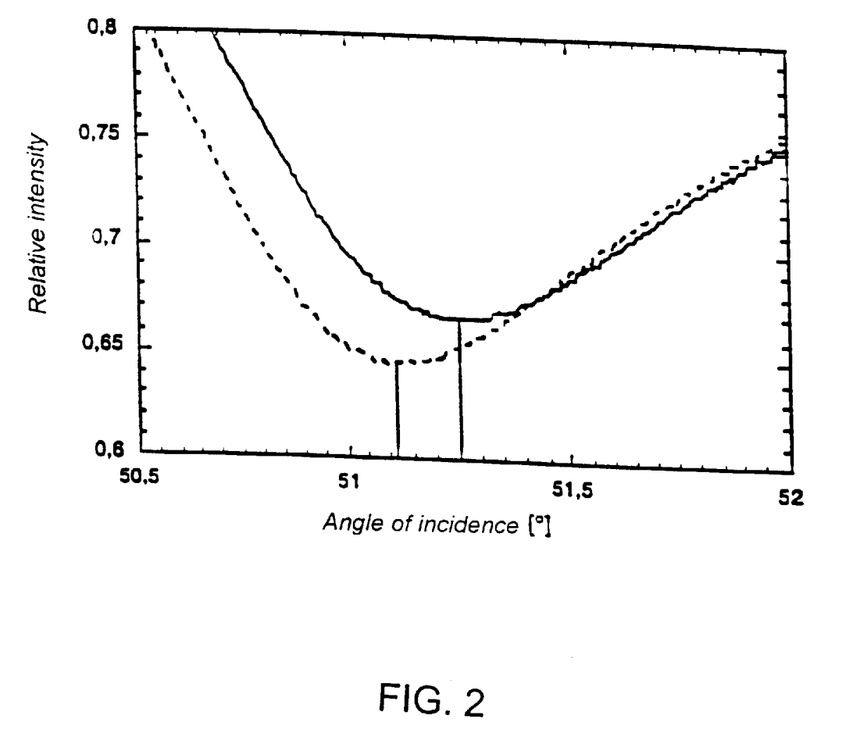
FIG. 2 shows the surface plasmon resonance curves before and after the bonding of bovine serum albumin to a carboxymethydextran-functionalized gold surface.

To activate the carboxyl groups of the dextran layer, the surface is brought into contact with 77 mg of EDC and 12 mg of NHS for 10 minutes. After this, a bovine serum albumin solution (BSA) (16.7 $\mu$mole·l$^{-1}$) is brought into contact with the surface. After 20 minutes the surface is rinsed with 1 ml of water and then with 1 ml of 0.01 mole·l$^{-1}$ hydrochloric acid to remove unspecifically bonded BSA. in a next step, a surface plasmon resonance measurement is performed to monitor the growth of the layer in thickness (cf. FIG. 2).

Example 2

A gold-coated glass support (film thickness: approx. 50 nm) is immersed for 12 h into a $2 \cdot 10^{-2}$ mole·l$^{-1}$ aqueous solution of mercaptoethanol. After thorough rinsing with ultrapure water, the support is placed into a freshly prepared titanium(IV)butoxide solution. This solution is prepared by adding 7 ml of water and 34 mg of titanium(IV)butoxide (Aldrich) to a mixture of 0.5 ml of ethanol and 0.5 ml of toluol, stirring continuously. After an immersion time of 10 minutes the support is washed with plenty of ultrapure water. After this, another functionalization step is performed using (3-(2,3-epoxypropoxy)propyl)triethoxy silan (Wacker GF 82).

For this functionalization, 7 ml of silan and 3 ml of H$_2$O are mixed, diluted with 190 ml of isopropanol and stirred at room temperature. The immersion time of the support in this solution is again 20 minutes. Next, the support is washed with plenty of ultrapure water and placed for 24 h in a 30 weight % solution of dextran (Dextran T500, Pharmacia) in water. After washing, the support is placed in a freshly prepared solution of bromoacetic acid in aqueous NaOH. This solution has a bromoacetic acid concentration of 1 mole·l$^{-1}$ and a NaOH concentration of 2 mole·l$^{-1}$. The immersion time is 20 h.

The carboxymethyl-functionalized sensor is mounted in the SPR instrument described in example 1. The sensor surface is activated for 10 minutes by incubation in an aqueous solution of 77 mg·ml$^{-1}$ of ethly-3-dimethylamino-propyl-carbodiimide and 12 mg/ml of N-hydroxysuccinimide.

For bonding of the receptor, a solution of protein A (10 $\mu$g·ml$^{-1}$) in a PBS buffer (0.15 mole·l$^{-1}$ NaCl, 0.38 mmole·l$^{-1}$ NaH$_2$PO$_4$·H$_2$O, 1.67 mmole·l$^{-1}$ Na$_2$HPO$_4$, pH 7.4) is applied to the surface pretreated in this way. The incubation time is 60 minutes. To deactivate carboxyl groups that are not reacted, incubation for 20 minutes with a 1 mole·l$^{-1}$ solution of ethanolamin in water is performed.

Figure 3:
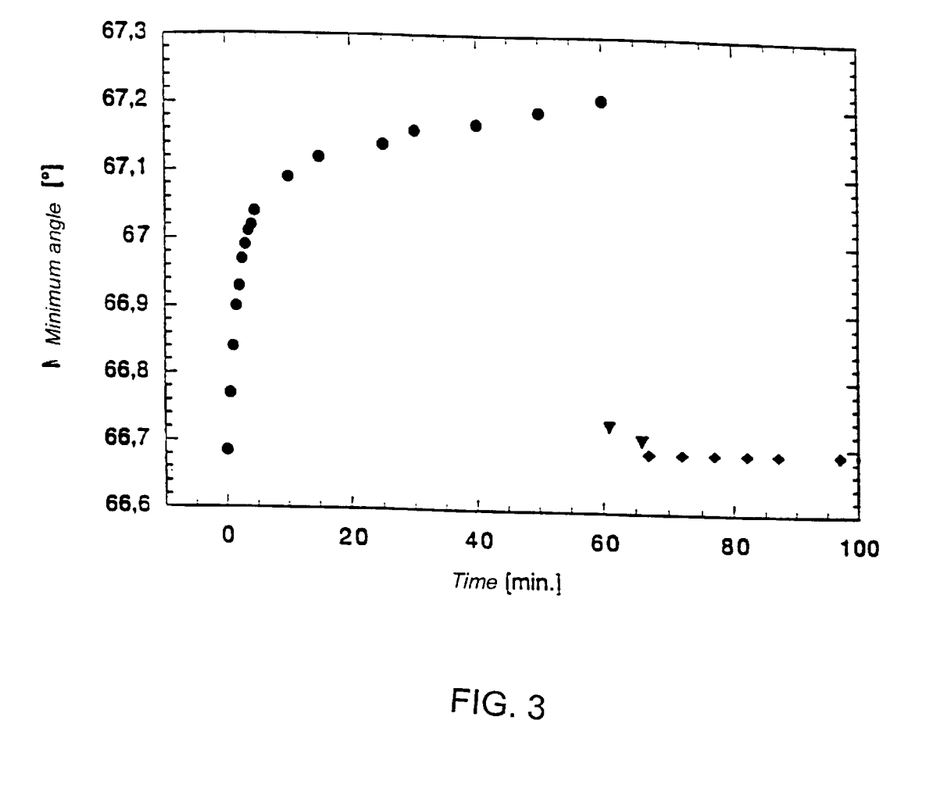
FIG. 3 shows the evolution of the minimum angle in surface plasmon resonance measurements with sheep-anti-mouse IgG solution and with bovine serum albumin solution.

After rinsing with the PBS buffer solution, the ligand/receptor interaction can be observed. For this, a solution of sheep-anti-mouse IgG (270 $\mu$g·ml$^{-1}$) in PBS buffer is brought into contact with the sensor surface. The time dependence of the sheep-anti-mouse IgG ligand bonding (circles) can be monitored by monitoring the position of the plasmon minimum in dependence of the time (FIG. 3). The shift of the minimum towards a higher incidence angle serves as an indicator for the growth of the layer in thickness.

After the bonding is completed, the sensor surface can be regenerated by rinsing it twice with diluted hydrochloric acid (triangles). A check measurement using a bovine serum albumin solution with a comparable concentration (270 $\mu$g·ml$^{-1}$) shows that the interaction with the sheep-anti-mouse IgG is a specific one: there is no bonding of the bovine serum albumin which has a very strong tendency to unspecific adsorption (lozenges).

What is claimed is:

1. A biosensor with a surface comprising a precious metal layer to which a hydrogel, a surfactant layer or biotin is bonded by means of a monolayer of organic molecules; whereby said organic molecules have the formula A—R—B, whereby A is an atom or group providing the bonding to the precious metal;

R is a branched-chain or straight-chain hydrocarbon chain with a chain length of 6 carbon atoms or less; whereby the hydrocarbon chain may be interrupted in up to two places each by a phenylene group or a heteroatom; and B is an atom or group providing the bonding to the hydrogel, the surfactant layer or the biotin;

characterized in that the monolayer of organic molecules is stabilized by hydrogen bonds, aromatic-aromatic interactions or covalent bonds.

2. The biosensor according to claim 1, wherein the precious metal is gold.

3. The biosensor according to claim 1, wherein A is a thiol, disulfide, selenide or diselenide group.

4. The biosensor according to claim 1, wherein R is an alkylene group with 6 carbon atoms or less.

5. The biosensor according to claim 1, wherein B is a hydroxyl, epoxide or amino group.

6. The biosensor according to claim 1, wherein the surfactant layer comprises cationic, anionic or zwitterionic surfaces.

7. The biosensor according to claim 1, wherein the hydrogel is a polysaccharide, a derivative thereof, or a swellable organic polymer.

8. The biosensor according to claim 7, wherein the hydrogel is a polysaccharide derivative which possesses hydroxyl, carboxyl, amino or carbonyl groups.

9. The biosensor according to claim 8, wherein the hydrogel is carboxymethyldextran.

10. The biosensor according to claim 1, wherein the hydrogel is directly bonded to the organic molecules of the formula A—R—B.

11. The biosensor according to claim 1, wherein the hydrogel, the surfactant layer or the biotin is bonded to the organic molecules of the formula A—R—B by means of a metal oxide-comprising interlayer.

12. A process for the preparation of a biosensor, comprising the preparation of a monolayer of organic molecules on a precious metal layer and bonding of a hydrogel, a surfactant layer or biotin to said monolayer; whereby the organic molecules have the formula A—R—B, with

- A is an atom or group providing the bonding to the precious metal;
- R is a branched-chain or straight-chain hydrocarbon chain with a chain length of 6 carbon atoms or less; whereby the hydrocarbon chain may be interrupted in up to two places each by a phenylene group or a heteroatom; and
- B is an atom or group providing the bonding to the hydrogel, the surfactant layer or the biotin;

characterized in that the monolayer of organic molecules is stabilized by hydrogen bonds, aromatic-aromatic interactions or covalent bonds.

13. The process according to claim 12, wherein the hydrogel is directly bonded to the organic molecules of the formula A—R—B.

14. The process according to claim 12, wherein the bonding of the hydrogel, the surfactant layer or the biotin to the monolayer is achieved by means of a metal oxide-comprising interlayer.

15. The process according to claim 14, wherein the metal oxide-comprising interlayer is prepared by a sol-gel process.

16. The biosensor according to claim 1, wherein the biosensor further contains a metal oxide-containing interlayer for stabilization of the monolayer of organic molecules.

17. The biosensor according to claim 1, wherein B is an amine group and the hydrogel is carboxyl-functionalized.

18. The biosensor according to claim 1, wherein B is an epoxide group and the hydrogel is carboxyl-functionalized.

19. The biosensor according to claim 1, wherein B contains a phenylene group.

20. The process according to claim 12, wherein B is an amine group and the hydrogel is carboxyl-functionalized.

21. The process according to claim 12, wherein B is an epoxide group and the hydrogel is carboxyl-functionalized.

22. The process according to claim 12, wherein B contains a phenylene group.

* * * * *

UNITED STATES PATENT AND TRADEMARK OFFICE
CERTIFICATE OF CORRECTION

PATENT NO. : 6,472,224 B1  Page 1 of 1
DATED : October 29, 2002
INVENTOR(S) : Wischeroff et al.

It is certified that error appears in the above-identified patent and that said Letters Patent is hereby corrected as shown below:

Column 9,
Line 19, between the 1$^{st}$ and 2$^{nd}$ diagram, please insert
-- Reaction scheme 3 gives examples of surfactant or biotin layers combined with a metal oxidecomprising interlayer. --.

Signed and Sealed this

Sixteenth Day of December, 2003

JAMES E. ROGAN
*Director of the United States Patent and Trademark Office*